United States Patent [19]
Brown

[11] Patent Number: 5,824,082
[45] Date of Patent: Oct. 20, 1998

[54] PATCH FOR ENDOSCOPIC REPAIR OF HERNIAS

[76] Inventor: Roderick B. Brown, 1920 N. Lakeshore Dr., Glenwood, Minn. 56334

[21] Appl. No.: 892,533

[22] Filed: Jul. 14, 1997

[51] Int. Cl.[6] .................................. A61F 2/02; A61F 2/06
[52] U.S. Cl. ................................... 623/11; 623/1
[58] Field of Search ............................. 623/11, 1

[56] References Cited

U.S. PATENT DOCUMENTS

| | | | |
|---|---|---|---|
| 5,397,331 | 3/1995 | Himpens et al. | 623/11 |
| 5,507,811 | 4/1996 | Koike et al. | 623/11 |
| 5,634,931 | 6/1997 | Kugel . | |

OTHER PUBLICATIONS

Roderick B. Brown, "Laparoscopic Hernia Repair: A Rural Perspective", Surgical Laparoscopy & Endoscopy, vol. 4, No. 2, pp. 106–109 ©1994.

*Primary Examiner*—Mary Beth Jones
*Assistant Examiner*—John M. Black
*Attorney, Agent, or Firm*—Haugen and Nikolai, P.A.

[57] ABSTRACT

A prosthesis for use in hernia repair surgery having a preformed prosthetic fabric supported along its periphery by shape memory alloy wire having a transformation temperature corresponding to normal body temperature allowing the prosthesis to be tightly rolled into a cylindrical configuration for delivery through a laparoscopic instrument and which deploys to a predetermined shape as it warms up to body temperature.

5 Claims, 2 Drawing Sheets

PATCH FOR ENDOSCOPIC REPAIR OF HERNIAS

BACKGROUND OF THE INVENTION

I. Field of the Invention

This invention relates to apparatus to be used in hernia repair surgery, and more particularly to a prosthetic hernia repair patch that can be rolled into a tube for laparoscopic delivery through a trocar and which deploys to a generally planar form when ejected from the trocar into the abdominal cavity.

II. Discussion of the Prior Art

Since 1991, I have performed numerous laparoscopic hernia repair procedures on inguinal, ventral, incisional and umbilical hernias with a great deal of success in terms of patient satisfaction. When compared to open surgery, those having the laparoscopic procedure experience significantly less pain and more rapid return to normal activity.

In carrying out those procedures, I initially used a prosthetic patch made at the time of surgery from a sterile, woven, polypropylene mesh material that I folded in half to create a double layer and then cut to size, typically a 6 cm by 9 cm rectangle. Sutures were used to join the four corners of the rectangle and two additional sutures were positioned approximately midway along the unfolded edge. A slit was then created between these two additional sutures which was designed to accommodate the inferior epigastric vessels. Following dissection of the hernia sac away from the ipsilateral testicle and cord structures, the creation of a peritoneal incision and the subsequent dissection of the peritoneal flap and hernia sac away from the hernia defect and surrounding fascia and cord structures, the patch was rolled into a tube and inserted into a trocar sleeve that was then introduced through a larger diameter trocar, and delivered into the peritoneal cavity. A laparoscopic forceps was then used to unfurl the patch and place it anterior to the hernia defect and around the inferior epigastric vessels with the mesh covering both the direct and indirect hernia spaces. The mesh patch would then be held in place by stapling or suturing it to underlying fascia. Subsequently, the peritoneum was closed over the patch so that the entire piece of mesh was covered thereby.

While the above procedure proved quite successful in terms of outcomes, the need to fabricate the mesh patch at the time of surgery, the later difficulty in unrolling and positioning the mesh patch material relative to the direct and indirect hernia spaces and the need to then staple or suture the mesh patch in place necessarily adds significantly to the time and expense required for carrying out the procedure.

A need, therefore, exists for a hernia patch to be used in laparoscopic surgery that is prefabricated to conform to anatomical structures, that readily deploys when released from a tubular laparoscopic introducer and which will remain in place without a need for stapling or suturing to underlying facie. The present invention fulfills that need.

SUMMARY OF THE INVENTION

The hernia repair patch of the present invention comprises a wire frame that can be of various designs including, but not limited to, the form of a closed loop where the wire comprising the frame is a shape memory alloy. A synthetic prosthetic material, such as woven polypropylene or expanded PTFE (Gortex), is attached to and supported by the wire frame. The wire frame supporting the mesh material may be formed from NiTiNOL or other suitable shape memory alloy and can be attached to the prosthetic material so that it has an hour-glass shape when the alloy is in its austenite form and a rolled, cylindrical shape when in a martensite form. The atomic percent of nickel in the alloy is such that the alloy exhibits a transformation temperature at about 37° C. (body temperature). Thus, when the patch is cooled, it can be readily formed into a cylindrical configuration for placement in a delivery trocar. When ejected out of the trocar into the patient's abdominal cavity, it warms to the point where the alloy is in its austenite form so that it springs into its functional, predetermined configuration. The narrowed central portion of an hour-glass shape patch accommodates the inferior epigastric vessels and cord structures while the opposed end lobes will cover the direct and indirect hernia space. Because the frame is integral to the patch, it does not migrate and, accordingly, need not be sutured or stapled in place. It remains anchored following its being covered by the peritoneum in a sandwich or laminated fashion.

The foregoing features, objects and advantages of the invention will become apparent to those skilled in the art from the following detailed description of a preferred embodiment, especially when considered in conjunction with the accompanying drawing.

DESCRIPTION OF THE PREFERRED EMBODIMENT

Figure 1:
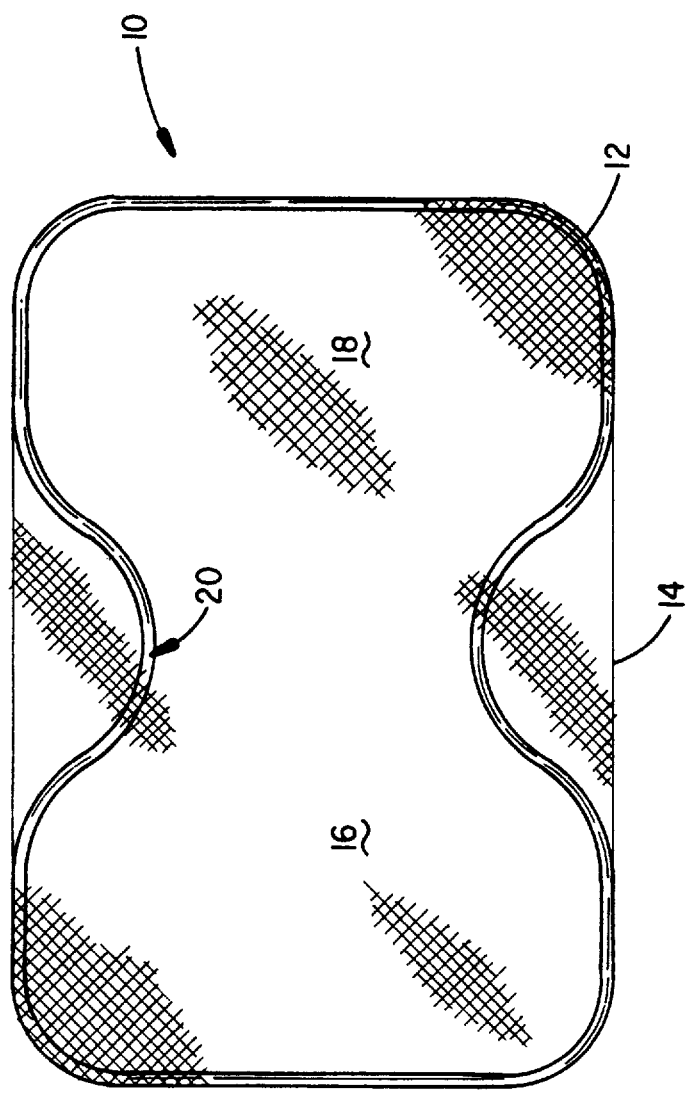
FIG. 1 is an enlarged plan view of the hernia repair patch constructed in accordance with the present invention.

Referring to FIG. 1, there is illustrated an enlarged view of a hernia repair patch constructed in accordance with the present invention. The patch prosthesis is indicated generally by numeral 10 and is seen to include an outer frame member 12 comprising a wire formed from a shape metal alloy, preferably a nickel titanium alloy comprising 49–51 atomic percent nickel and the remainder titanium. Such an alloy is commonly referred to as NiTiNOL. By proper adjustment of the relative concentration of nickel in the alloy, the wire frame 12 can be made to exhibit a transition temperature between the austenite form and the martensite form at about 37° C. corresponding to body temperature. The wire is shown as comprising a closed loop which is generally oval in shape, but with a constricted minor axis creating an hour-glass shaped profile. While this shape is perhaps preferred, the invention need not be limited to this shape configuration and the frame need not be a closed loop.

Supported within the wire frame 12 is a prosthetic fabric 14, preferably woven strands of polypropylene plastic or expanded PTFE (Gortex). As such, the prosthetic device 10 may be steam sterilized. In use, the lobes 16 and 18 are adapted to be positioned over the direct and the indirect hernia spaces, respectively, and when this is done, the constricted central portion, indicated generally by numeral 20, will allow placement without interference with the inferior epigastric vessels.

Figure 2:
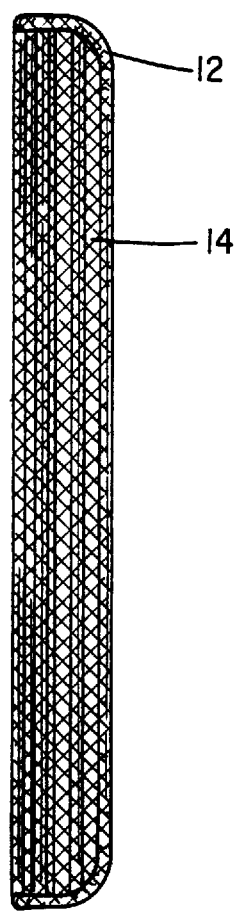
FIG. 2 shows the patch of FIG. 1 in a rolled, tubular configuration for endoscopic delivery through a trocar.
Figure 3:
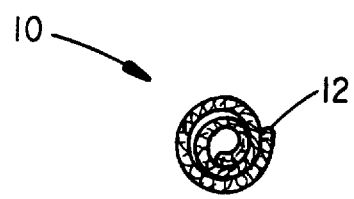
FIG. 3 is an end view of the rolled patch of FIG. 2.

When the alloy frame 12 is cooled below the transformation state of the shape memory alloy so that it is in its martensite form, the prosthesis 10 can be helically wrapped to form a cylindrical structure as illustrated in FIGS. 2 and 3. This allows the prosthesis to be introduced into the abdominal cavity through a tubular trocar. As the shape memory alloy frame 12 warms up to body temperature, it transforms to its austenite form as depicted in FIG. 1. Using a laparoscopic forceps, the prosthesis 10 of FIG. 1 can be grasped and repositioned by the surgeon until the lobes 16 and 18 and the narrowed center section 20 are appropriately located for covering the hernia defect.

Those skilled in the art will appreciate that the prosthesis may be manufactured in a variety of shapes and sizes to accommodate children, adults, males and females and especially the type of hernia encountered. It can be contained in a sterile pack until ready for use. While NiTiNOL is the preferred shape memory alloy, other alloys, such as gold-cadmium, nickel-aluminum and manganese-copper would also be suitable. Moreover, the prosthetic fabric material 14 need not be polypropylene mesh, but can also comprise other suitable materials, such as body-compatible biaxially oriented polymeric films.

Without limitation, the major axis of the prosthesis 10 may be in a range of from about 6–12 cms and the constricted minor axis may be about 4–8 cms. Such device can be tightly rolled into a cylinder, as shown in FIG. 2, so as to fit within the internal lumen of a 10 mm or smaller trocar or introducer sheath.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A hernia repair patch comprising:

(a) a wire frame formed from a shape memory alloy wherein the wire frame has an hour-glass shape when the shape memory alloy is in a austenite form and a rolled compact shape when in a martensite form; and (b) a prosthetic fabric material attached to and supported along a periphery thereof by said frame.

2. The hernia repair patch of claim 1 wherein the shape memory alloy comprises NiTi with a percentage of Ni in the alloy in a range of from 49 to 51 atomic percent.

3. The hernia repair patch of claim 2 wherein the shape memory alloy exhibits a transformation temperature of about 37° C.

4. The hernia repair patch as in any one of claims 1, 2 or 3 in which the prosthetic fabric material is selected from a group consisting of a woven mesh of polypropylene fibers and expanded PTFE.

5. The hernia repair patch as in claim 1 wherein the prosthetic fabric material is generally planar and has a major longitudinal dimension in a range of from 6 to 12 cm and a minor transverse dimension in a range of from 4 to 8 cm.

* * * * *